(12) United States Patent
Mori

(10) Patent No.: US 8,303,637 B2
(45) Date of Patent: Nov. 6, 2012

(54) CATHETER FOR TOPICAL COOLING AND TOPICAL COOLING DEVICE USING THE SAME

(76) Inventor: Atsuo Mori, Kumagaya (JP)

(*) Notice: Subject to any disclaimer, the term of this patent is extended or adjusted under 35 U.S.C. 154(b) by 1131 days.

(21) Appl. No.: 12/167,846

(22) Filed: Jul. 3, 2008

(65) Prior Publication Data

US 2008/0275535 A1 Nov. 6, 2008

Related U.S. Application Data

(62) Division of application No. 10/518,370, filed as application No. PCT/JP03/07609 on Jun. 16, 2003, now abandoned.

(30) Foreign Application Priority Data

Jun. 17, 2002 (JP) ................................. 2002-175423

(51) Int. Cl.
*A61F 7/12* (2006.01)
(52) U.S. Cl. .......................... 607/105; 607/104; 607/107
(58) Field of Classification Search ........... 607/104–107
See application file for complete search history.

(56) References Cited

U.S. PATENT DOCUMENTS

| 3,125,096 A | 3/1964 | Antiles |
| 5,269,758 A | 12/1993 | Taheri |
| 6,019,783 A | 2/2000 | Philips et al. |
| 6,146,411 A | 11/2000 | Noda et al. |
| 6,149,624 A | 11/2000 | McShane |
| 6,379,331 B2* | 4/2002 | Barbut et al. ............... 604/113 |
| 6,527,798 B2* | 3/2003 | Ginsburg et al. ............ 607/106 |
| 6,610,083 B2 | 8/2003 | Keller et al. |
| 6,699,269 B2* | 3/2004 | Khanna ....................... 607/105 |
| 7,077,825 B1 | 7/2006 | Stull |
| 2002/0068964 A1 | 6/2002 | Dobak, III |
| 2003/0060864 A1 | 3/2003 | Whitebook et al. |

FOREIGN PATENT DOCUMENTS

| JP | 8-299376 A | 11/1996 |
| JP | 2002-500915 A | 1/2002 |
| JP | 2002-507453 A | 3/2002 |
| WO | 99/37226 A1 | 7/1999 |
| WO | WO 99/37226 A1 | 7/1999 |
| WO | WO 99/48449 A1 | 9/1999 |
| WO | 99/66970 A1 | 12/1999 |
| WO | 00/38601 A1 | 7/2000 |
| WO | WO 00/51669 A1 | 9/2000 |
| WO | 02/13710 A1 | 2/2002 |

\* cited by examiner

*Primary Examiner* — Roy Gibson
(74) *Attorney, Agent, or Firm* — Sughrue Mion, PLLC

(57) ABSTRACT

Topical cooling of spinal cord, brain, esophagus, etc. can be selectively and continuously carried out under convenient control without causing any changes in internal pressure of spinal cord cavity, brain pressure, etc. by inserting a catheter, which has no hole connecting to the outside and in which a heat- cooling medium is circulated in its inner space to thereby cool a topical site; into the spinal cord, the epidural cavity, the subdural cavity or the subarachnoid cavity of the brain or the esophageal cavity and placing therein and then circulating the heat/cooling medium within the inner space of the catheter.

8 Claims, 9 Drawing Sheets

FIG. 2
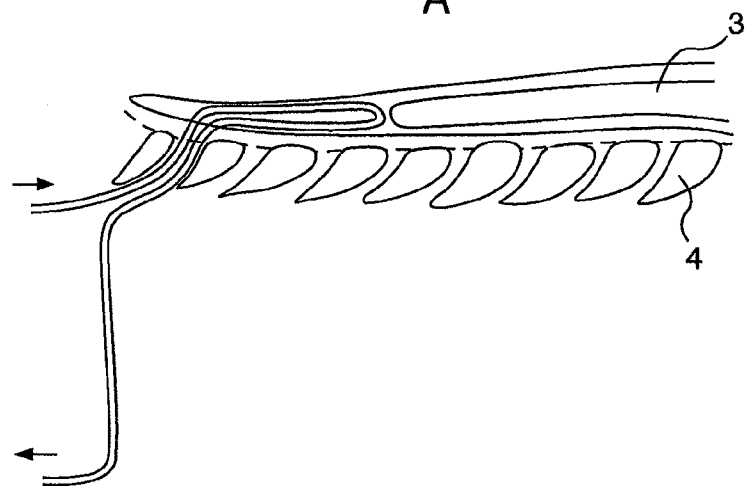
A
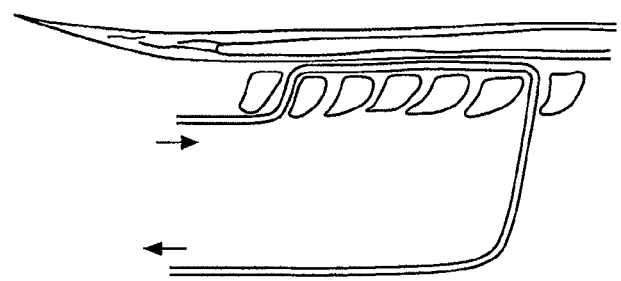
B
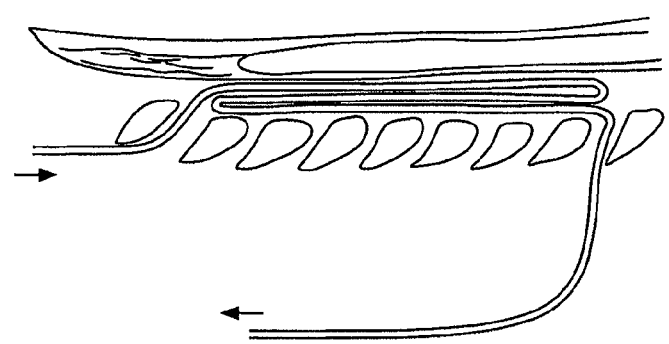
C

FIG. 3
A
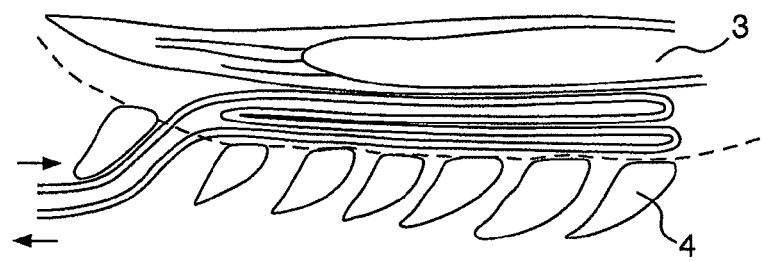
B
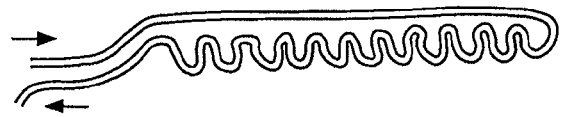
C
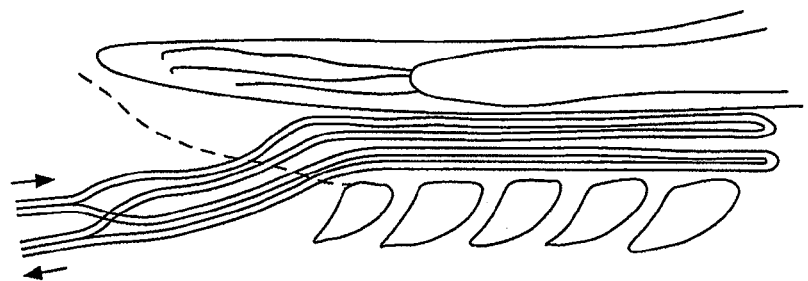

FIG. 6
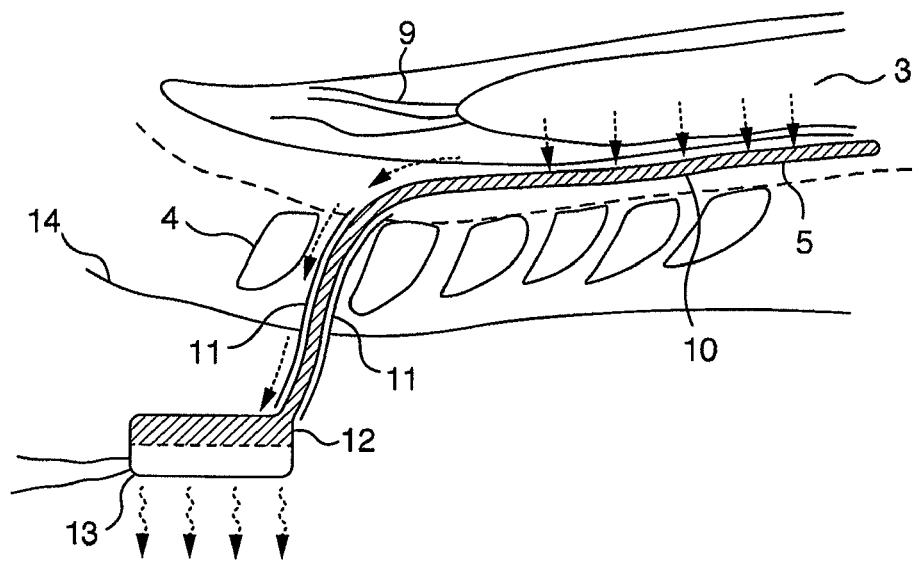
A
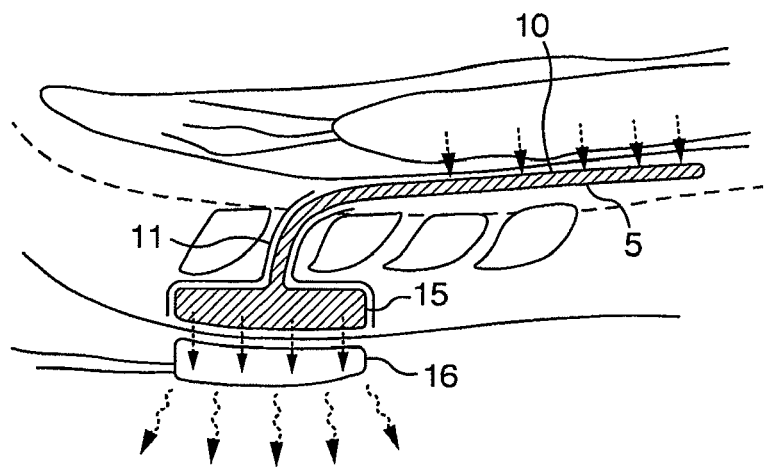
B

CATHETER FOR TOPICAL COOLING AND TOPICAL COOLING DEVICE USING THE SAME

This is a divisional of application Ser. No. 10/518,370 filed Dec. 17, 2004, now abandoned which is a National Stage Application filed under §371 of PCT Application No. PCT/JP03/07609 filed Jun. 16, 2003, which claims priority from Japanese Patent Application No. 2002-175423 filed on Jun. 17, 2002. The entire disclosures of the prior applications are considered part of the disclosure of the accompanying divisional application and are hereby incorporated by reference.

TECHNICAL FIELD

The present invention relates to a catheter for topical cooling and a topical cooling device using the same for topical cooling of organs or tissues of mammals including human on a continual basis. More specifically, the present invention relates to a catheter that is orally or transnasally inserted into the epidural cavity, the subdural cavity, or the subarachnoid cavity of the spinal cord or the brain, or the esophageal cavity and placed therein, which is a topical cooling catheter for topically cooling the spinal cord, the brain or the esophagus selectively and continuously by circulating a heat-cooling medium in its inner space, and a topical cooling device that employs said catheter. Furthermore, it relates to a topical cooling device composed of a material having a high thermal conductivity and comprising a heat absorption member in the form of a catheter, a heat insulation member, and a heat radiation member, wherein the heat absorption member in the form of a catheter is inserted into an organ or a tissue of a mammal including a human and placed therein to thereby cool a topical site selectively and continuously by absorbing heat from the heat absorption member and radiating heat from the heat radiation member.

BACKGROUND ART

Paraplegia is a serious complication thought to occur in 5-20% of surgery cases due to defective circulation of the spinal root arteries, the nutrient vessels of the spinal cord, at the time of surgery for thoracoabdominal aortic aneurysm. When the thoracic aorta is blocked at ordinary temperature, it is believed, irreversible damages of spinal nerves develop in about one hour (Svensson L G, Crawford E S, Hess K R, Coselli J S, Safi H J. Experience with 1509 patients undergoing thoracoabdominal aortic operations. J Vasc Surg 1993; 17:357-70). However, during operations, it is very difficult to specify the spinal root arteries from a multitude of intercostal arteries, and its reconstruction often takes a lot of time.

Clinical tests and studies have already demonstrated that maintaining a low body temperature by central cooling with an artificial heart and lung during operations is useful for spinal cord protection (Kouchoukos N T, Wareing T H, Izumoto H, et al., Elective hypothermic cardiopulmonary bypass and circulatory arrest for spinal protection during operations on the thoracoabdominal aorta. J. Thorac Cardiovasc Surg 1990, 99:659-64). However, systemic hypothermia may disadvantageously induce demerits such as abnormal coagulation and respiratory disorders due to extracorporeal circulation. At present, there are no methods that can completely avoid the occurrence of paraplegia associated with surgery for the thoracoabdominal aortic aneurysm.

As methods of topical cooling of the spinal cord, there have been reported a method in which two catheters are separately inserted to the subarachnoid cavity (the spinal cord cavity) (one for injection that injects cooling water, and the other for discharging for use in the drainage of the cooling water) and topical cooling is accomplished under perfusion of the spinal cord (Paul A., Spinal cord protection during thoracoabdominal aneurysm resection. J. Thorac Cardiovasc Surg 1995, 109:1244-6). With this method, however, when the drainage of the cooling water becomes poor, internal pressure of the subarachnoid cavity may be excessively enhanced which may cause serious complications such as cerebral hernia, and thus its clinical application was difficult. Furthermore, Cambria of Harvard Univ. has reported a method in which a catheter was transdermally inserted in the surgery of thoracoabdominal aortic aneurysm, through which a cooling water was continuously injected, and during one operation about 1400 ml of physiological saline was injected without drainage and allowed to diffuse as it is without drainage (Cambria R P, Davidson J K, Zannetti S et al., Clinical experience with epidural cooling for spinal cord protection during thoracic and thoracoabdominal aneurysm repair. J. Vasc Surg 1997, 25:234-43; Cambria R P, Davidson J K. Regional Hypothermia for Prevention of Spinal Cord Ischemia complications after thoracoabdominal aortic surgery: Experience with epidural cooling. Seminars in Thoracic and Cardiovascular Surgery, Vol. 10, No. 1 (January), 1998, pp. 61-65). With this method, however, due to the cooling water injected, internal pressure of the subarachnoid cavity may be excessively enhanced leading to about twice the normal internal pressure of the medullary cavity, and thus because of potential risk of ischemic disorders such as cerebral hernia and reduced perfusion pressure, the method has not been adopted in other facilities. Furthermore, experimentally, although there has been reported a method of injecting a bolus of cooling saline into the subdural cavity, the method does not permit the continuous cooling of the spinal cord for a long time. These two methods have been developed for the cooling of the spinal cord in the operation room, it is necessary to inject the cooling water into the epidural cavity while monitoring internal pressure of the subarachnoid cavity and intraspinal temperature so that internal pressure of the subarachnoid cavity may not be excessively enhanced. Thus, since the methods are troublesome in management, and the amount induced into the epidural cavity is limited, it is not amenable to continuous cooling for a long time in intensive care units or general hospital wards.

On the other hand, traumatic brain contusion is caused by traffic accidents or accidents, and significantly affects the mortality and morbidity of those involved, posing a serious social problem as well. The general hypothermic therapy for traumatic brain contusion has a concept that nerve cells that were damaged, specifically those cells that received medium irreversible damages, which may be considered to be a penumbra retaining a potential of recovery, present in the periphery of nerve cells that received irreversible damages are protected by a nerve cells-protecting effect retained by hypothermia so as to improve the prognosis and QOL of the patient. Its usefulness has already been recognized and has been put into clinical practices such as in the form of surface-cooling the entire body with a blanket at a medium body temperature of about 32° C. (Jiang J., yu M., Zhu C., Effect of long-term mild hypothermia therapy in patients with severe traumatic brain injury: 1-year follow-up review of 87 cases. J. Neurosurge. 2000, 93(4):546-9). However, there are demerits such as decreased immune functions associated with maintaining the hypothermia of the entire body, and the resulting infections, arrhythmia or abnormal coagulation. In particular, it has been pointed out, when the patient is an elderly, demerits such as infections associated with the hypothermia of the entire body becomes pronounced leading to the onset of complications, with a result that the overall survival is not improved. Also in order to overcome the demerits such as infections, arrhythmia and abnormal coagulation, complicated management of the entire body at the intensive care unit is required causing economic problems that more labor and cost are required. Specifically, when the treatment is prolonged, the brain hypothermia therapy that maintains the hypothermia of the entire body requires an enormous personnel and economic costs.

Also, there is a need for the development of devices for topical cooling the esophagus as a means of preventing esophageal injuries that may occur as a complication at the time of radiofrequency ablation for the atrium performed as a method of treatment of atrial fibrillation.

DISCLOSURE OF THE INVENTION

Thus, it is an object of the present invention to provide a catheter that is applied into the epidural cavity, the subdural cavity, or the subarachnoid cavity to cool the spinal cord continuously, wherein the spinal cord can be cooled safely, selectively and continuously without injecting any liquid into the epidural cavity, the subdural cavity, or the subarachnoid cavity, the spinal cord is free from any risk such as ischemic injuries, paraplegia occurring after a thoracoabdominal aortic surgery can be prevented, or the selective and continuous cooling of the spinal cord for a long time can be attained, and management thereof is easy, and a device using the same for cooling the spinal cord selectively and continuously.

It is another object of the present invention to provide a catheter for cooling the brain continuously and topically wherein the brain alone can be selectively and continuously cooled while maintaining at an ordinary temperature, demerits of maintaining the hypothermia of the entire body while maintaining the brain-protecting effect of the brain hypothermia can be overcome, and a higher survival and an improved degree of disturbance of consciousness can be attained, and a cooling device using the same.

Furthermore, it is an object of the present invention to provide a catheter for cooling the esophagus topically and continuously wherein it is possible to topically cool the esophagus selectively and it is also possible to relieve complications as a means for preventing esophagus injuries that may occur at the time of radiofrequency ablation of the atrium performed as a treatment of atrial fibrillation at the clinical setting, and a cooling device using the same.

Thus, the present invention is a topical cooling catheter that has an inner space to circulate a heat-cooling medium therein, has no hole connecting to the outside, and is composed of a high thermal conductivity, said catheter being inserted into organs or tissues of mammals including humans and placing therein thereby to topically cool them selectively and continuously. Preferably, it is a cooling catheter that is transdermally inserted into the epidural cavity, the subdural cavity, or the subarachnoid cavity of the spinal cord or the brain, or the esophageal cavity and placed therein so as to topically cool the spinal cord or the brain selectively and continuously, or that is a topical cooling catheter that is orally or transnasally inserted into the esophagus and placed therein so as to topically cool the esophagus selectively and continuously.

Also the present invention is a topical cooling device comprising a reservoir for preserving a heat-cooling medium, a pump for delivering said heat-cooling medium, a heat exchanger for cooling said heat-cooling medium, and the above catheter, wherein these are linked and arranged in series by a pipe-shaped tube for circulating said heat-cooling medium.

Furthermore, it is a topical cooling device composed of a material having a high thermal conductivity comprising a heat absorption member in the form of a catheter, a heat insulation member, and a heat radiation member, wherein the heat absorption member in the form of a catheter is inserted into an organ or a tissue of a mammal including a human and placed therein to thereby cool a topical site selectively and continuously by absorbing heat from the heat absorption member and radiating heat from the heat radiation member. Preferably, it is a cooling catheter that is transdermally inserted into the epidural cavity, the subdural cavity, or the subarachnoid cavity of the spinal cord or the brain, or the esophageal cavity and placed therein so as to topically cool the spinal cord or the brain selectively and continuously, or that is a topical cooling catheter in which the heat absorption member in the form of a catheter is orally or transnasally inserted into the esophagus and placed therein so as to topically cool the esophagus selectively and continuously.

BRIEF EXPLANATION OF THE DRAWINGS

FIG. 2 is a drawing wherein various catheters of the present invention in which a heat-cooling medium is circulated were applied to the spinal cord. A is a catheter inserted into the subarachnoid cavity, B is a catheter inserted into the epidural cavity so that the inlet and the outlet be separate from each other. and C is a catheter inserted into the epidural cavity so that the inlet and the outlet be separate from each other and was folded back in a zigzag configuration.

FIG. 3 is a drawing wherein various catheters of the present invention in which a heat-cooling medium is circulated were applied to the spinal cord. A is a catheter of which inlet and outlet were inserted at one site into the epidural cavity and which was folded back in a zigzag configuration, 3 is the spinal cord, 4 is spinous process of vertebra, B is a catheter of which inlet and outlet were laterally folded back at one site in a zigzag configuration, and C is two sets of catheters arranged in parallel and inserted into the epidural cavity.

FIGS. 6a and 6b are drawings wherein a device of the present invention containing a catheter in which a heat-cooling medium is not circulated was applied to the spinal cord. 3 is the spinal cord, 4 is spinous process of vertebra, 5 is a cooling catheter, 9 is a cauda equina, 10 is a heat absorbing member, 11 is a heat insulation member, 12 is a heat radiation member, 13 is a cooling device, 14 is the skin, 15 is a subcutaneous heat radiation member, and 16 is a cooling device. Arrows in the broken line represent the direction of heat flow.

BEST MODE FOR CARRYING OUT THE INVENTION

Figure 1:
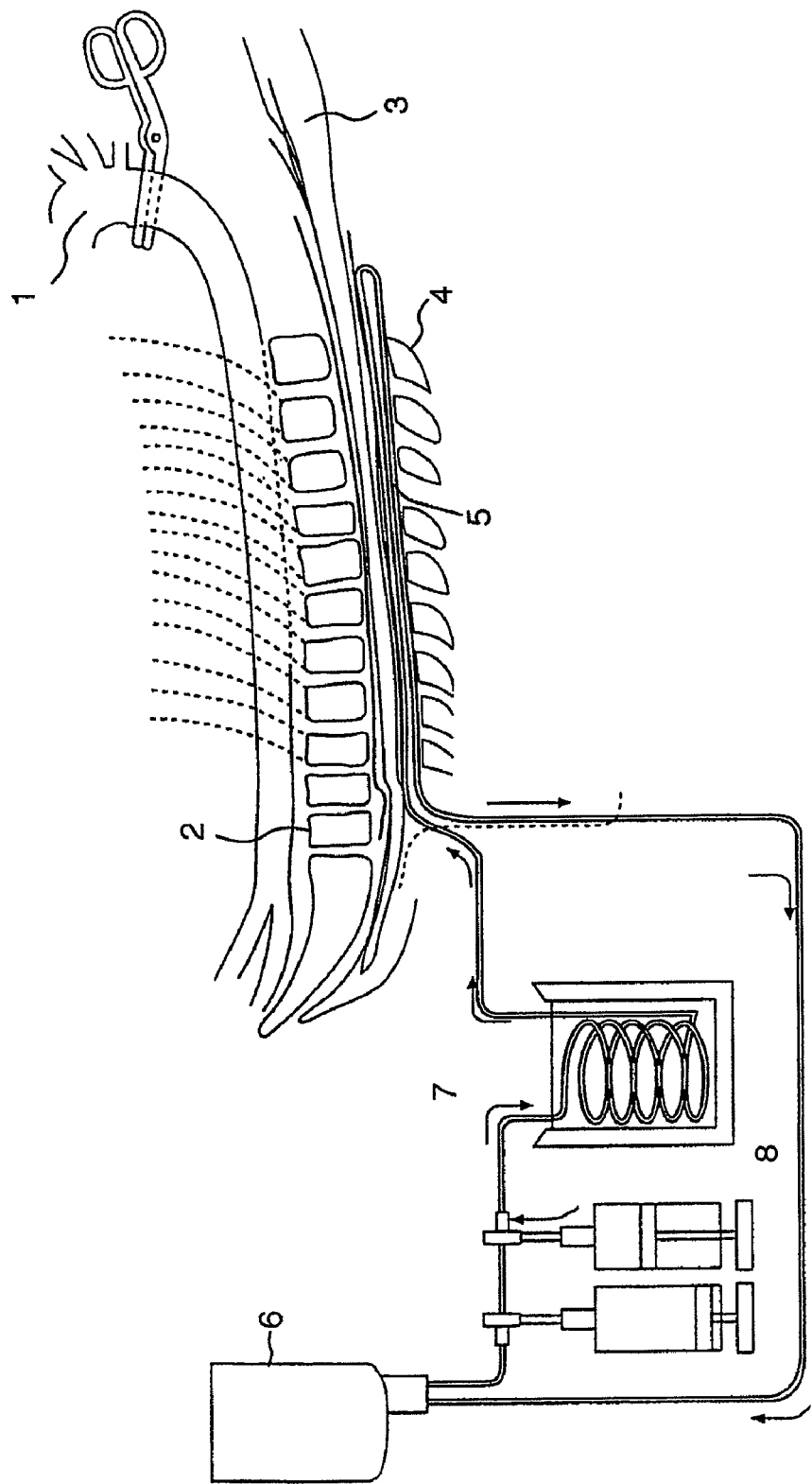
FIG. 1 is a drawing wherein a catheter of the present invention in which a heat-cooling medium is circulated and a device of the present invention were applied to the spinal cord. 1 is an aorta, 2 is the vertebral body, 3 is the spinal cord, 4 is spinous process of vertebra, 5 is a catheter placed, 6 is a reservoir, 7 is a heat exchanger, and 8 is a pump.

The catheter of the present invention for topical cooling and a device using the same are intended for topical cooling selectively and continuously by inserting a catheter that has no hole connecting to the outside into an organ or a tissue of a mammal including a human and placed therein, and a heat-cooling medium such as a cooling water is circulated in the catheter to thereby absorb heat from a topical site of the organ or the tissue. Also, the topical cooling device of the present invention is composed of a heat absorption member, a heat insulation member and a heat radiation member, in which the heat absorption member in the form of a catheter is inserted into the organ or the tissue and placed therein and, without circulating a heat-cooling medium such as a cooling water, heat is absorbed from the heat absorption member in the form of a catheter and radiated from the heat radiation member thereby to topical cool it selectively and continuously.

Hereinbelow, the catheter of the present invention in which a heat-cooling medium is circulated for topical cooling and a device using the same, as well as a device in which a heat-cooling medium is not circulated for topical cooling are explained in detail.

First, the catheter of the present invention in which a heat-cooling medium is circulated for topical cooling and a device using the same is explained.

The catheter of the present invention in which a heat-cooling medium is circulated for topical cooling is usually inserted transdermally into the epidural cavity, the subdural cavity, or the subarachnoid cavity of the spinal cord or the brain by laminectomy or the puncture to the epidural cavity, the subdural cavity or the subarachnoid cavity, or a combination of the two of them using a puncture needle. Generally the epidural cavity, and the subdural cavity of the spinal cord and the brain are a narrow cavity with a thickness of about 1-2 mm and a width of about 7-9 mm, but they are surrounded by smooth fibrous connecting tissues such as the dura mater and the yellow ligament, which is why a catheter can be inserted therein. Also, in the case of the subarachnoid cavity of the spinal cord and the brain, insertion can be made into a space of the second lumber vertebra or lower. In order to topical cool the esophagus, a catheter is inserted orally or transnasally into the esophagus cavity.

The catheter of the present invention is a thin tubing made of a material having an essentially high thermal conductivity, for example a metal such as stainless, titanium, aluminum, gold, silver, and copper, and serve as a heat-cooling medium. It must have an inner space in which a liquid such as distilled water or a gas such as carbon dioxide can circulate. Generally, its inner diameter is about 05-0.8 mm and the outer diameter is 0.8-1.2 mm. The both ends of the catheter have a connecting member capable of connecting to a pipe-shaped tubing so as to form a circuit. The catheter is inserted into the epidural cavity, the subdural cavity, or the subarachnoid cavity of the spinal cord or the brain, or the esophagus by laminectomy or the puncture of the epidural cavity at 1 or 2 sites. When insertion is made at one site, the catheter is preferably shaped in a folded-back U form, and form the apex of the folded-back U form, insertion is made. When insertion is made at two sites, the inlet and the outlet are separately present in the catheter, which may be folded back in a zigzag configuration. Also, the two sets of catheters may be arranged in parallel and placed in the epidural cavity, the subdural cavity, or the subarachnoid cavity and placed therein. When the brain is cooled, a disk-shaped or whirl-shaped catheter is preferred.

Figure 4:
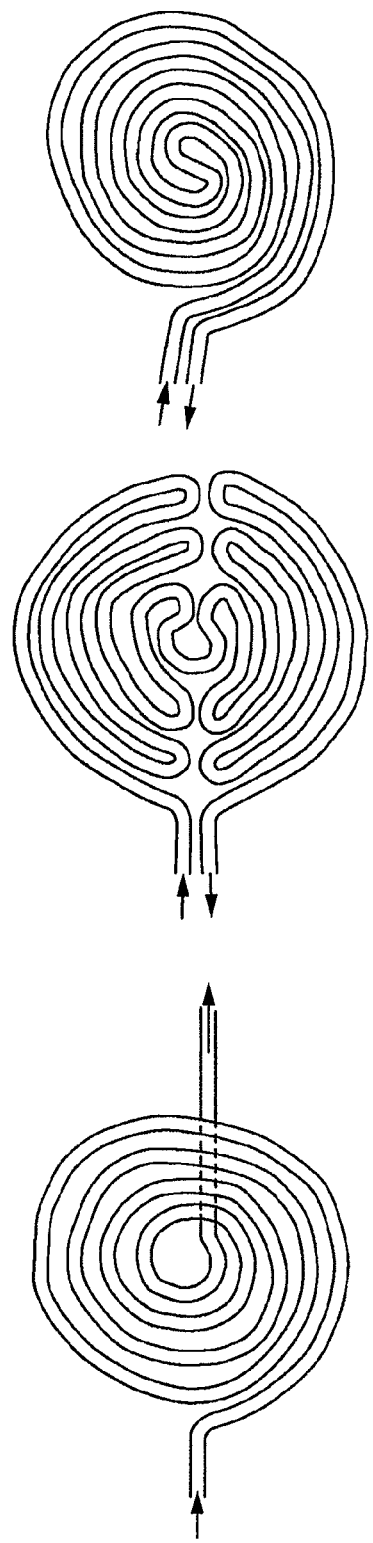
FIG. 4 represents various catheters for use in the cooling of the brain. Arrows in the Figure may be in the opposite direction.
Figure 5:
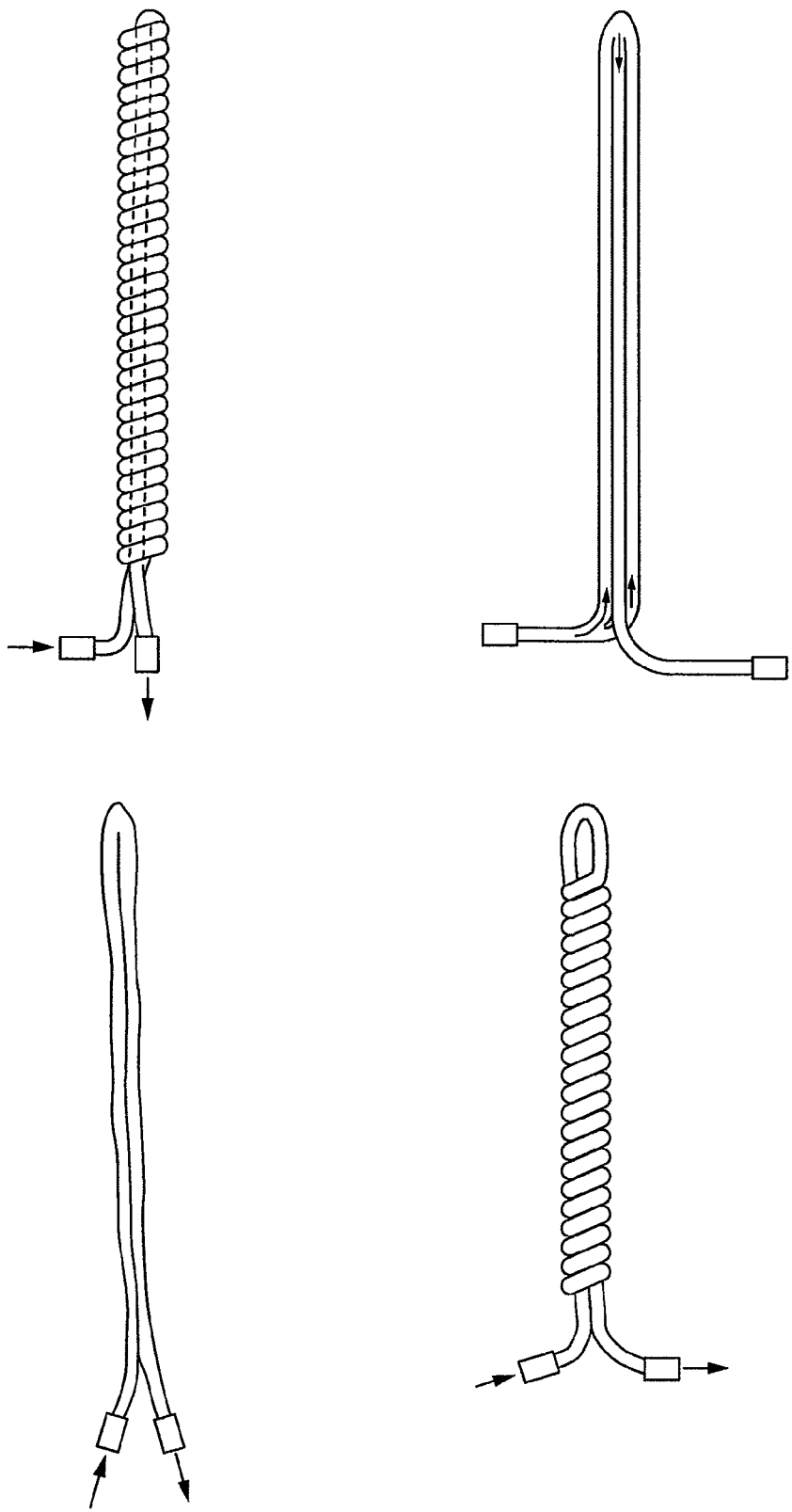
FIG. 5 represents various catheters for use in the cooling of the spinal cord and esophagus. Arrows in the Figure may be in the opposite direction.

FIG. 1 shows a state in which a U-shaped catheter of the present invention has been inserted into the epidural cavity of the spinal cord and placed therein. FIG. 2 shows a catheter a U-shaped catheter inserted into the subarachnoid cavity of the spinal cord in the upper part, a catheter inserted into the epidural cavity of the spinal cord so that the inlet and the outlet are separate in the middle part, and a catheter inserted into the epidural cavity of the spinal cord and folded back in a zigzag form at the lower part. FIG. 3 shows a catheter in which the inlet and the outlet have been inserted into the epidural cavity at one site and which has been folded back in a zigzag form at the upper part, a catheter in which the inlet and the outlet have been inserted into the epidural cavity at one site and which has been folded back laterally in a zigzag form at the middle part, and two sets of catheters arranged in parallel and inserted into the epidural cavity at the lower part. FIG. 4 shows various catheters Formula (I) the cooling of the brain. FIG. 5 shows various catheters for use in cooling the esophagus. The catheters shown in FIG. 5 may also be used as catheters for use in cooling the spinal cord.

The catheter of the present invention has no holes connecting to the outside. Thus, it is not a catheter for injecting a cooling water into the epidural cavity, subdural cavity, the subarachnoid cavity, or the esophagus cavity, but it cools the spinal cord, the brain, and the esophagus by absorbing heat from the surface of the catheter in contact with the dura mater or from the surface of the catheter placed in the subarachnoid cavity or the esophagus cavity, or across the dura mater, or directly cool the spinal cord, the brain and the esophagus. Since the catheter is thin, it easily reaches the same temperature as the spinal cord etc. if it is only placed therein, whereas the catheter of the present invention can be kept at low temperature due to the circulation of the heat-cooling medium in the inner space, thereby enabling to keep the spinal cord, the brain, the esophagus etc. continuously at low temperature and protecting them. Furthermore, since the catheter of the present invention is made of a material having a high thermal conductivity, the effect of radiating heat extracoporally due to the heat conductivity of the catheter per se can be expected, and the spinal cord, the brain, the esophagus etc. can be efficiently and continuously cooled. With a catheter made of a material such as polyurethane and silicone having a low thermal conductivity, efficient absorption of heat from the spinal cord, the brain, the esophagus etc. would be difficult, in which case by thinning the thickness of the catheter, the thermal conductivity thereof can be enhanced and thereby can be used in the present invention.

As a variation of the catheter of the present invention, it may be a catheter in which a film made of a material having a high thermal conductivity such as a gold foil, a silver foil, an aluminum foil etc. has been attached in between the catheters such as a folded back U-shaped catheter. Furthermore, it may be a catheter on which an insulating film has been attached to the side corresponding to the opposite side of the dura mater. With a catheter to which such an insulating film has been attached, the contact area between the catheter and the dura mater or the spinal meanings becomes increased thereby enabling a more efficient cooling of the spinal cord. Also, the cooling efficiency can also be enhanced by attaching a thin semiconductor that can be cooled such as a Peltier device in between the U-shaped catheters.

The topical cooling device of the present invention is composed of the four units including the above catheter of the present invention and a pipe-shaped tubing connecting them. As shown in FIG. 1, the four units are a reservoir 6 for storing a heat-cooling medium, a pump 8 for delivering a heat-cooling medium such as a liquid and a gas, a heat exchanger 7 for cooling the heat-cooling medium, and the above-mentioned catheter 5, and these four are arranged in a series association. By circulating a heat-cooling medium, for example a liquid such as distilled water or a gas such as carbon dioxide, though the pipe-shaped tubing and the four units, heat is absorbed from the spinal cord 3, the brain, the esophagus etc. through the surface of the catheter 5 placed in the epidural cavity, the subdural cavity, or the subarachnoid cavity of the spinal cord or the brain, and thus a continuous topical cooling can be realized.

Each of the units is explained below. First, in the reservoir 6, a fixed amount of a liquid such as distilled water or a gas such as carbon dioxide that represents a heat-cooling medium is stored. This is to deal with changes in the flow rate associated with the passage of time by storing a fixed amount of a medium circulating through the circuit. Since it is a circulating type, there is no concern that the medium leaks more than the amount stored in the reservoir 6 in case a leak occurred in the circuit, and thus it also plays a role of a safety unit.

Then, for the pump 8 for delivering a heat-cooling medium such as a liquid or a gas, this is a unit that emits a liquid or a gas representing a heat-cooling medium, and circulate it through the circuit. Since the catheter 5 usually has a thin diameter, the pump 8 is preferably one that can withstand high pressure such as a syringe pump or a high-pressure roller pump. Furthermore, when the heat-cooling medium is a gas, a high-pressure cylinder may be substituted. The flow rate of the pump is, for example, about 20-30 ml/min when the heat-cooling medium is distilled water.

The cooling heat exchanger 7 is a unit that renders the temperature of the heat-cooling medium low while it passes through the unit. For example, there can be mentioned a cooling device that cools the outside of the spiral metal circuit with crushed ice. In addition to them, any unit that can cool can be used, for example, a semiconductor such as a Peltier device, a cooling gas etc.

By circulating a heat-cooling medium through the device composed of the four units, i.e. the reservoir 6, the pump 8, the cooling heat exchanger 7 and the catheter 5, it becomes possible to topically cool the spinal cord, the brain, the esophagus etc. continuously for a long time without injecting any cooling water into the epidural cavity, the subdural cavity, the subarachnoid cavity, the esophagus cavity or the like, thus without increasing the internal pressure of the subarachnoid cavity.

Nextly, the device of the present invention that cools the spinal cord, the brain, the esophagus etc. without circulating a heat-cooling medium is explained below.

The device of the present invention that cools the spinal cord, the brain, the esophagus etc. without circulating a heat-cooling medium is made of a material having a high thermal conductivity, and is composed of a heat absorption member in the form of a catheter, a heat insulation member, and a heat radiation member, wherein the heat absorption member in the form of a catheter is inserted into the epidural cavity, the subdural cavity, the subarachnoid cavity, the esophagus cavity or the like and placed therein to thereby cool a topical site selectively and continuously by absorbing heat from the heat absorption member and radiating heat from the heat radiation member.

An example of a case wherein such a device was applied to the spinal cord is shown in FIG. 6. As to the shape of the catheter of such a device, it may be the same as the above catheter for circulating the heat-cooling medium, and preferably the overall shape is, for example, a pipe, a bar, a plate, a disk, or a swirl. In the case of a pipe, it is usually preferred that the outer diameter is about 0.5-2.0 mm, in the case of a plate, it is usually preferred that the thickness is preferably about 0.1-2.0 mm and the width is about 2-8 mm, and the length is about 3-30 cm. In the case of a disk, it is usually preferred that the diameter is about 4-10 cm and the thickness is about 1-2 mm. As is also shown in FIG. 6, the cooling device of the present invention is composed of a heat absorption member 10 in the form of a catheter 5, a heat insulation member 11, and a heat radiation member 12. The heat absorption member 10 in the form of a catheter is a part that is inserted into the epidural cavity, the subdural cavity, the subarachnoid cavity of the spinal cord or the brain, the esophagus cavity or the like, and placed therein so as to absorb heat from the spinal cord, the brain, the esophagus etc. from across the dura mater, or by a direct contact with the spinal cord, the brain, the esophagus etc. The shape of the heat absorption member in the form of a catheter is usually a pipe, a bar, a plate, a disk, or a swirl. The heat absorption member is composed of a material having a high thermal conductivity, and as such a material there can be preferably mentioned gold, silver, copper, an aluminum alloy, titanium and the like. When the heat absorption member is a plate, it is preferred that the surface of the side opposite to the side in contact with the spinal cord, the brain, the esophagus etc. has been insulated so that heat is not lost from the tissues other than the spinal cord, the brain, the esophagus etc. It is because there occurs no wasteful heat exchange with the surrounding tissues other than the spinal cord etc. As materials for insulation, specifically there can be mentioned silicone, polyurethane, rubber, and the like.

The heat insulation member 11 is a middle part of a cooling device that is not in contact with the spinal cord, the brain, the esophagus etc., and it is preferred that the central part thereof is made of gold, silver, copper, an aluminum alloy, titanium and the like. The shape is similar to that of the heat absorption member, and the length depends on the distance between the heat absorption member and the heat radiation member. In order to avoid wasteful heat exchange between the heat insulation member and the adjacent tissues, the outside thereof is preferably insulated so as to cover the central part. As materials for insulation, specifically there can be mentioned silicone, polyurethane, rubber, and the like. The heat insulation member is a part that transports heat from the heat absorption member to the heat radiation member depending on the temperature difference between the heat absorption member and the heat radiation member.

The heat radiation member 12 is a part in which heat transmitted from the heat absorption member of the catheter is forcefully radiated, and thus a larger surface area is preferred. For example, as shown in FIG. 6, the heat radiation member 12 is a plate, and one side of this plate is preferably a radiation surface that is not insulated. The heat radiation surface of such a plate heat radiation member may be cooled by a cooling unit 13 that performs cooling with ice or a cooling gas, or may be cooled by connecting it to a heat exchanger, or may be forcefully air-cooled by intensely blowing the air. Alternatively, the surface may be forcefully cooled with a cooling unit having a cooling surface such as a Peltier device. The heat radiation member may be placed extracorporally or subcutaneously. The size and shape of the heat radiation member are, but not limited to, preferably, for example, a square of 5×5 cm to 10×10 cm. When it is placed subcutaneously, it is implanted so that the heat radiation surface is directly under the dermis, and by sandwiching the dermis with an extracorporal cooling unit such as ice, a cooling gas, a Peltier device etc., heat is radiated from the subcutaneous cooling surface to an extracorporal cooling unit such as ice, a cooling gas, a Peltier device etc. In this case, since the catheter does not extracorporally protrudes through the skin, it has an advantage that a risk of infection etc. may be reduced. When it is placed subcutaneously, the surface opposite to the dermis is preferably insulated so that wasteful heat exchange does not occur with the surrounding tissue. As materials for insulation, specifically there can be preferably mentioned silicone, polyurethane, rubber, and the like.

As mentioned above, in the device of the present invention, heat absorbed at the heat absorption member from the spinal cord, the brain, the esophagus etc. passes through the heat insulation member to the subcutaneous heat radiation member, from which the heat is continuously absorbed by a cooling unit or a heat exchanger, or the surrounding air, with a result that the spinal cord, the brain, the esophagus etc. can be continuously and selectively cooled. Furthermore, since there is no cooling water injected to the epidural cavity, the subdural cavity, the subarachnoid cavity, the esophagus cavity or the like, there is no fear of increasing the internal pressure of the subarachnoid cavity.

The catheter of such a device, as with a catheter in which a heat-cooling medium is circulated in the inner space for topical cooling, may be inserted transdermally into the epidural cavity, the subdural cavity, or the subarachnoid cavity by laminectomy or the puncture to the epidural cavity, the subdural cavity or the subarachnoid cavity, or a combination of the two of them using a puncture needle, or orally or transnasally into the esophagus cavity, and placed therein to cool the spinal cord, the brain, the esophagus etc.

The present invention will now be explained in further details with reference to Examples, but it should be noted that the present invention is not limited to these examples in any way.

EXAMPLE 1

Cooling of the Spinal Cord Using the Catheter of the Present Invention and a Device Using the Same and Their Effects The device of the present invention was applied to a porcine survival model in order to examine the effect of protecting the spinal cord. Thus, while blocking the descending aorta of a porcine survival model with a blocking clamp for 30 minutes, the device of the present invention was used in which the catheter was placed in the epidural cavity and distilled water was circulated through the catheter, the spinal cord was topical cooled, and the effect of protecting the spinal cord on the porcine survival model was evaluated by a neurological score. In the experiment, changes in the spinal cord somatosensory evoked potential (sSSEP) with time was monitored, and the effect of protecting the spinal cord was evaluated. sSSEP is an electrophysiological test of the spinal nerve termed as the spinal cord-induced potential, and specifically it is a test in which a stimulus by the stimulatory sSSEP electrode that was transmitted to the center (the direction of the cerebra) via the sensory nerves of the spinal cord is picked up by a detecting sSSEP electrode to investigate the function of the sensory nerves of the spinal cord.

1. Experimental Method

As the experimental animal, pigs weighing about 30 kg were used. After intramuscular injection of ketamine 15 mg/kg, a venous line was secured in the marginal ear vein. After tracheostomy was performed and a tracheal tube was inserted, controlled respiration was started using a respirator. For the maintenance of anesthesia, the depth of anesthesia was controlled with nitrous oxide and halothane. An arterial line was secured at the right axillary artery and electrocardiogram (ECG) was continuously monitored. Using a temperature sensor, the temperature of the spinal cord, the epipharynx and the rectum was monitored.

Pigs were placed in a lateral position to shave the back. At the height of the third lumber vertebra and the seventh thoracic vertebra, laminectomy was performed, and the catheter for topical cooling of the device of the present invention shown in FIG. 1 was transdermally inserted into the epidural cavity by epidural cavity puncture using a puncture needle. After confirming that the waveform of sSSEP can be reproducibly detected, the posture was changed to the dorsal position. After abdominal section at the center line, a hole was made in the aortic hiatus and thoracic descending aorta was taped.

Distilled water was circulated through the catheter for topical cooling of the present invention for 60 minutes, and after the spinal cord was cooled and heparin 5 ml was intravenously injected, the thoracic descending aorta was blocked at the distal position of the left subclavian artery with a blood vessel clamp.

While measuring sSSEP, the thoracic descending aorta was blocked at the distal position of the left subclavian artery for 30 minutes, and the spinal cord was made ischemic to determine changes. After removal of blocking, the thorax was closed.

After removing the catheter for cooling and the sSSEP electrodes, the wound was closed, and after awakening from anesthesia, the tracheal tube was removed, and the neurological status of the lower limb to 48 hours post-operation was evaluated according to the Tarlov score.

A similar experiment was performed without circulating distilled water through the catheter for topical cooling of the device of the present invention and with the spinal cord at an ischemic sate, sSSEP and the neurological status were evaluated.

Then, the pigs were anesthetized by a bolus intravenous injection of pentobarbital and a KCl solution.

2. Experimental Result

1) Changes In and Effect of sSEP by the Device of the Present Invention Under the Aortic Blocking First, placing the sSSEP electrode for epidural cavity placing for stimulation and detection from the laminectomy site, highly reproducible and stable sSSEP was detected in all animals.

In the experiment group in which the topical cooling of the spinal cord was performed by the device of the present invention, there were no changes in wave height even 30 minutes after blocking of sSSEP in four of seven cases. In three cases, decreases in wave height of sSSEP started at 20-25 minutes after blocking of the thoracic descending aorta, but no disappearances in wave height occurred even 30 minutes after blocking. The amplitude of sSSEP after removal of blocking of the thoracic descending aorta exhibited a recovery of 89+/−7% as compared to before blocking. During the 20 minutes when the aorta was pre-cooled with PCEC without blocking the aorta, no significant changes in amplitude were noted in sSSEP.

In the control group in which distilled water was not circulated through the catheter for topical cooling of the present invention placed in the epidural cavity, decreases in wave height and changes into such as a biphase occurred at about 10 minutes after the blocking of the thoracic descending aorta in all seven cases, and about 15-20 later sSSEP disappeared. In the control group, the amplitude of sSSEP after removing the blocking of the thoracic descending aorta remained a recovery of 55+/−6% as compared to that before blocking.

2) Evaluation of Neurological Status of the Spinal Cord after Ischemic Stress

For neurological findings of pigs, the experimental animal, after operation, the motor function of the lower limb were evaluated using the Tarlov's score. The result is shown in Table 1.

TABLE 1

|  | The experiment group by the device of the present invention (n = 7) | | | The control group (n = 7) | | |
| --- | --- | --- | --- | --- | --- | --- |
|  | 12 hours later | 24 hours later | 48 hours later | 12 hours later | 24 hours later | 48 hours later |
| Tarlov 5 | 5 | 7 | 7 | 0 | 0 | 0 |
| Tarlov 4 | 2 | 0 | 0 | 0 | 0 | 0 |
| Tarlov 3 | 0 | 0 | 0 | 0 | 0 | 0 |
| Tarlov 2 | 0 | 0 | 0 | 0 | 1 | 1 |
| Tarlov 1 | 0 | 0 | 0 | 3 | 2 | 2 |
| Tarlov 0 | 0 | 0 | 0 | 4 | 4 | 4 |

Tarlov's score is a method for evaluating the motor function of the lower limb that was established in order to evaluate stages in grades with 5 representing a complete recovery and 0 representing a complete paraplegia. As can be clearly seen from the result in Table 1, in the experiment group in which the topical cooling of the spinal cord was performed by the device of the present invention, five cases of seven exhibited a complete recovery (Tarlov score 5) and two cases exhibited a recovery of 4 in Tarlov score. In the control group in which distilled water was not circulated through the catheter, four cases of seven exhibited a complete paraplegia (Tarlov score 0) and two cases exhibited an incomplete paraplegia (Tarlov score 1). Statistically, the experiment group with the invention device has given a significantly better neurological scores than the control group (p<0.05). Thus, the protective effect against ischemic injuries of the spinal cord by the device of the present invention was demonstrated.

3) Effect of Cooling the Spinal Cord by the Device of the Present Invention

Figure 7:
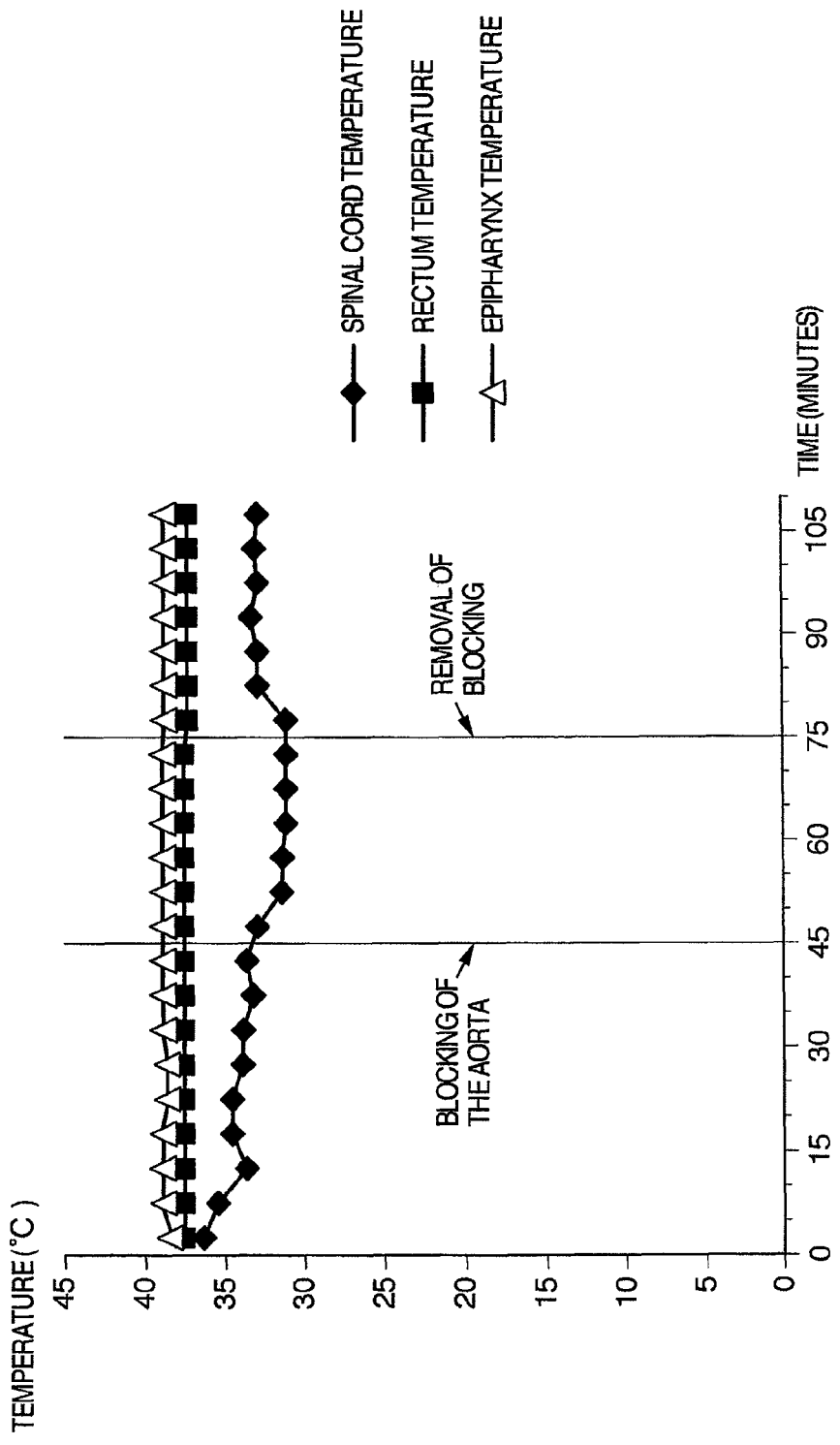
FIG. 7 is a graph showing an effect of cooling the spinal cord by a device of the present invention containing a catheter in which a heat-cooling medium is circulated in its inner space.

Changes in the temperature of the spinal cord, the epipharynx and the rectum with time when the spinal cord was cooled by the device of the present invention are shown in FIG. 7. As can be seen from the graph in FIG. 7, by cooling with the device of the present invention, only the temperature of the spinal cord decreased by about 5° C. about 10 minutes later. In contrast, the temperature of the rectum and the epipharynx did not change. Then, after removing the blocking of the aorta, the temperature of the spinal cord increased by about 2° C., and after cessation of cooling, the temperature of the spinal cord became the same as those of the rectum and the epipharynx in about 5 minutes. From these results, it was demonstrated that the spinal cord is selectively cooled.

Figure 8:
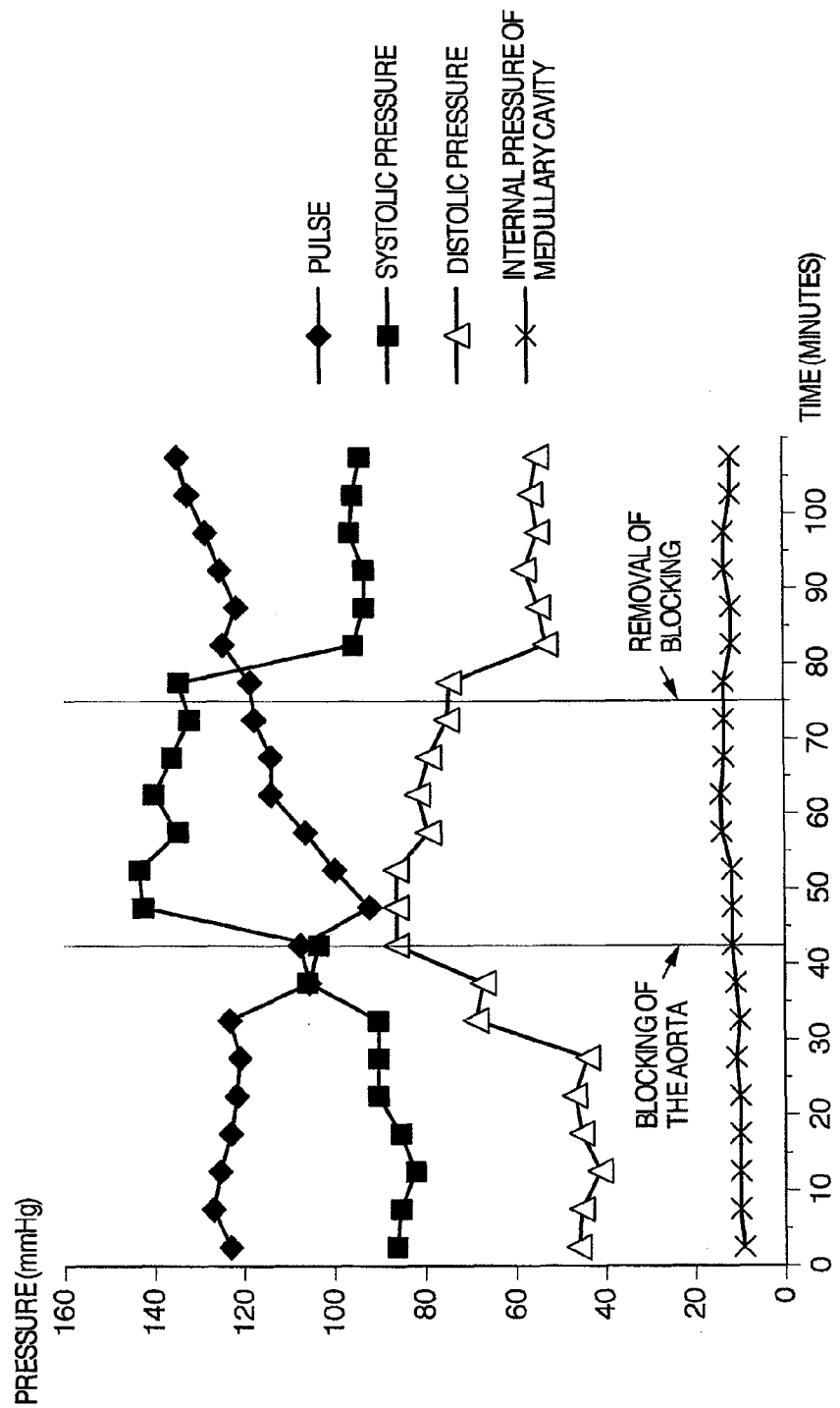
FIG. 8 is a graph showing changes in changes in pressure of the medullary cavity by a device of the present invention containing a catheter in which a heat-cooling medium is circulated in its inner space.

4) Changes in Internal Pressure of the Subarachnoid Cavity of the Spinal Cord by the Device of the Present Invention Changes with time in internal pressure of the subarachnoid cavity of the spinal cord, pulses, the systolic pressure and the diastolic pressure during the period of cooling the spinal cord by the device of the present invention are shown in FIG. 8. As can be seen from the graph in FIG. 8, since no cooling water is injected into the epidural cavity in the device of the present invention, no changes in internal pressure of the subarachnoid cavity of the spinal cord occurred after cooling. Furthermore, by the blocking of the thoracic descending aorta, the systolic pressure and the diastolic pressure increased and pulses decreased slightly. After removing the blocking of the aorta, the systolic pressure and the diastolic pressure returned to the original values.

3. Discussion

The above-mentioned experiment clarified the following two points.

Firstly, since paraplegia by the blocking of the thoracic descending aorta for 30 minutes could be avoided by the effect of cooling the spinal cord by the device of the present invention, it was demonstrated that the device of the present invention has a spinal cord protecting effect in the survival model. As shown in Table 1, six cases of seven in the control group were paraplegia or incomplete paraplegia, whereas in the experiment group in which topical cooling was performed by the device of the present invention, all cases after awakening from anesthesia were able to stand up on its own. This indicates that the cooling of the spinal cord by the device of the present invention is promising as a means for avoid paraplegia that is accompanied with surgery for thoracoabdominal aortic aneurysm in clinical settings. Thus, it can be expected that the spinal cord alone is selectively cooled while maintaining the other organs at ordinary temperature, and during the blocking of the aorta, time to anastomose more intercostal arteries to artificial blood vessels and to reconstruct them can be secured.

It was demonstrated that the effect of sSSEP can be further increased under the condition of the aorta being blocked, and the spinal cord can be cooled to 30.5° C., 7° C. lower than the body temperature. This result can be explained as follows. Thus, it is believed that when the cooling of the spinal cord was performed by the device of the present invention under a normal condition, the temperature of the spinal cord tissue is moved to the direction of being increased by the blood and of being decreased by the cooling catheter. At the condition in which the aorta is blocked, it is speculated that blood flow to the spinal cord tissue decreased, and the force of increasing the tissue temperature weakened with a result that the cooling effect by the cooling catheter was higher during blocking. By rendering the spinal cord at a low temperature, the metabolism of the nerve cells should be further inhibited and a more potent protective effect should be expected. Clinically, it can be expected that while maintaining the other organs at ordinary temperature, and during the blocking of the aorta, time to anastomose more intercostal arteries to artificial blood vessels and to reconstruct them can be secured.

Secondly, with the blocking of the aorta, the control group has exhibited a decrease and disappearance of the wave height of sSSEP and an incomplete recovery after removal, whereas in the group in which the spinal cord was cooled by the device of the present invention, sSSEP due to the epidural cavity electrode stimulation—the epidural cavity electrode derivation did not disappear, and recovered almost completely 30 minutes after removing the blocking. What is interesting is that sSSEP does not change greatly by the cooling of the spinal cord alone by the device of the present invention before blocking the aorta. This may be considered advantageous since in the clinical setting it also means that sSSEP can be used during cooling to judge whether the reconstruction of the spinal cord root arteries is sufficient or not.

Also, the result is very interesting that sSSEP does not change for about 20 minutes even if the aorta is blocked during cooling. This result would be explained as follows. Thus, by blocking the aorta, the supply of oxygen and energy to the spinal cord decreased, while the metabolism of the spinal cord was inhibited by topical cooling and the demand for oxygen and energy of the spinal cord tissue was also inhibited, which means a well balanced state meaning no insufficient metabolism. Thus, under an environment of moderate hypothermia, it is believed, sSSEP can be used as an index showing a balance sheet of metabolism rather than an index showing the blood flow of the spinal cord tissue.

The above-mentioned experiment demonstrated the most important problem that the cooling of the spinal cord by the device of the present invention can actually protect the spinal cord from disorders derived from ischemia. By rendering sSSEP the epidural cavity electrode stimulation—the epidural cavity electrode detection, it became a highly sensitive index having a reliability and a reproducibility. Also, it was also shown, using a survival model, to have a neurologically protective effect as well.

EXAMPLE 2

Cooling of the Brain Using the Catheter of the Present Invention and a Device Using the Same and Their Effects An experiment was carried out in which during the operation of cerebral decompression, a catheter in a swirl form having no hole connecting to the epidural cavity was placed in the epidural cavity of the brain, and a cooling water was circulated through this catheter to absorb heat from the surface of the brain to topically cool the brain selectively and continuously.

1. Experimental Method

As the experimental animal, pigs weighing about 35-40 kg were used. After intramuscular injection of ketamine 15 mg/kg, a venous line was secured in the marginal ear vein. After a tracheal tube was inserted, controlled respiration was started using a respirator. For the maintenance of anesthesia, the depth of anesthesia was controlled with nitrous oxide and isoflurane. An arterial line was secured at the right axillary artery and electrocardiogram (ECG) was continuously monitored. Using a temperature sensor, the temperature of the rectum and the epipharynx was monitored.

Pigs were placed in a lateral position to shave the head, and then the scalp and the subcutaneous tissue were dissected to expose the cranial bone. The cranial bone in the forehead was cut to a circle with a diameter of about 4 cm to expose the dura mater of the parietal lobe from the frontal lobe. To the exposed dura mater was contacted the cooling surface in a disk form made by rendering the catheter in a swirl form. Into the subdural cavity, a brain pressure sensor and a temperature sensor for determining the internal pressure of the subarachnoid cavity were placed to determine the brain temperature.

For 10 minutes a cooling water was circulated through the catheter for topical cooling, and the brain was topical cooled while determining the brain temperature. The circulation of the cooling water was stopped to confirm when the brain temperature becomes enhanced. After removing the catheter for cooling, the wound was closed, and the animals were euthanatized by a bolus intravenous injection of pentobarbital and a KCl solution.

2. Experimental Result

Figure 9:
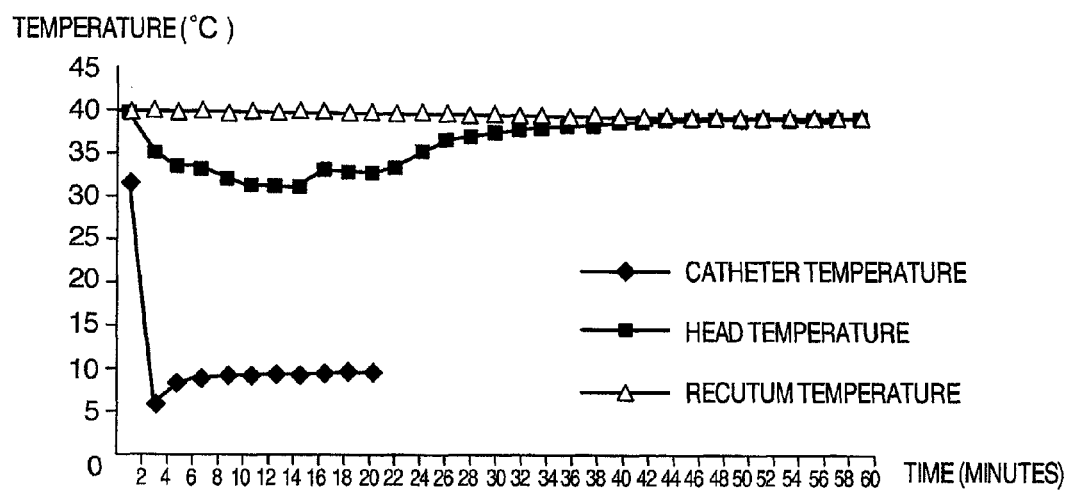
FIG. 9 is a graph showing an effect of cooling the brain by a device of the present invention containing a catheter in which a heat-cooling medium is circulated in its inner space.

The result on the effect of cooling the brain by the device of the present invention is shown in FIG. 9. As can be seen from FIG. 9, in about 5 minutes after starting cooling the temperature dropped from 39.7° C. to 31.2° C., indicating the reduction in temperature of about 8.5° C. in the brain temperature than the rectum temperature. During this time, the temperature of the rectum did not change despite the reduction in the temperature of the brain. During the cooling by the device of the present invention, the temperature of the brain was kept at about 8.5° C. lower than that of the rectum. After stopping cooling by the device of the present invention, the temperature returned to the temperature of the brain in about three minutes.

3. Discussion

From the above experiment, it can be expected that by the effect of cooling by the device of the present invention, the damaged brain tissue alone can be selectively cooled while keeping other organs at ordinary temperature. It was demonstrated that the brain tissue around the catheter can be cooled to 30° C. or lower which is about 7° C. lower than the body temperature.

EXAMPLE 3

Cooling of the Esophagus Using the Catheter of the Present Invention and a Device Using the Same and Their Effects An experiment was carried out in which a U-shaped catheter having no hole connecting to the esophagus cavity was orally placed in the esophagus, and a cooling water was circulated through this catheter to absorb heat from the surface of the esophagus to topically cool the esophagus selectively and continuously.

1. Experimental Method

As the experimental animal, pigs weighing about 35-40 kg were used. After intramuscular injection of ketamine 15 mg/kg, a venous line was secured in the marginal ear vein. After a tracheal tube was inserted, controlled respiration was started using a respirator. For the maintenance of anesthesia, the depth of anesthesia was controlled with nitrous oxide and isoflurane. An arterial line was secured at the right axillary artery and blood pressure was monitored. By monitoring an electrocardiogram continuously, the temperature of the rectum and the epipharynx was monitored.

Pigs were placed in a lateral position, and then intercostal chest opening was performed by postero-lateral thoracotomy to expose the esophagus. A U-shaped catheter having no hole connecting to the esophagus cavity was orally placed in the esophagus, and a cooling water was circulated through this catheter to absorb heat from the surface of the esophagus to topically cool the esophagus selectively and continuously. A needle-shaped temperature sensor was punctured through the right thoracic cavity to determine the temperature of the esophagus.

Twenty minutes later, a cooling water was circulated through the catheter for topical cooling, and the esophagus was topical cooled while determining the esophagus temperature. The circulation of the cooling water was stopped to confirm whether the esophagus temperature becomes enhanced. After removing the catheter for cooling, the wound was closed, and the animals were euthanatized by a bolus intravenous injection of pentobarbital and a KCl solution.

2. Experimental Result

Figure 10:
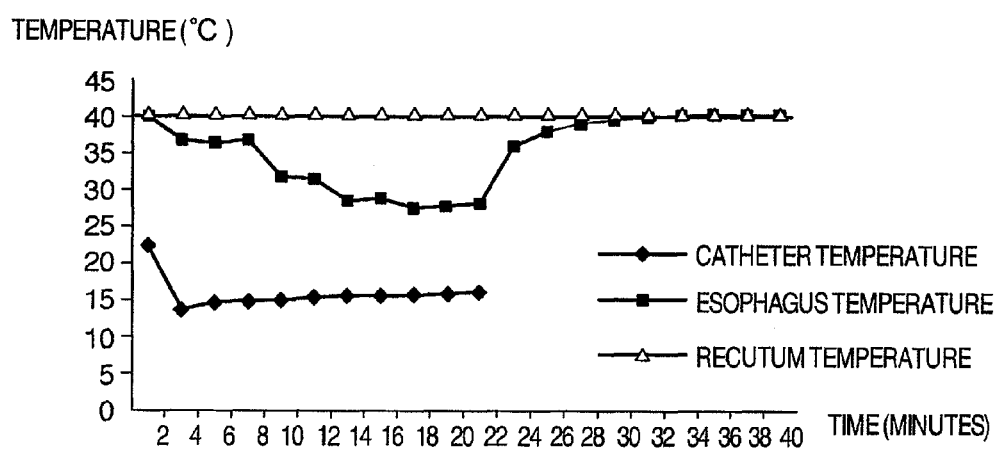
FIG. 10 is a graph showing an effect of cooling the esophagus by a device of the present invention containing a catheter in which a heat-cooling medium is circulated in its inner space.

The result on the effect of cooling the esophagus by the device of the present invention is shown in FIG. 10. As can be seen from FIG. 10, in about 20 minutes after starting cooling the temperature dropped from 39.7° C. to 28.1° C., indicating the reduction in temperature of about 11.6° C. in the esophagus temperature than the rectum temperature. During this time, the temperature of the rectum did not change despite the reduction in the temperature of the esophagus. During the cooling by the device of the present invention, the temperature of the esophagus was kept at about 11° C. lower than that of the rectum. After stopping cooling by the device of the present invention, the temperature returned to the temperature of the esophagus in about eight minutes.

INDUSTRIAL APPLICABILITY

As has been explained in detail above, the catheter and the device of the present invention have the following advantages, and thus are industrially highly applicable.

First of all, what is different from other methods of cooling the epidural cavity is that since no liquid is injected into the epidural cavity, the subdural cavity, or the subarachnoid cavity, cooling can be continued for a long time without increasing the internal pressure of the medullary cavity or the brain pressure, and thus the spinal cord or the injured cerebrum can be selectively topical cooled.

Second is a point that it is a device that can cool the spinal cord or the injured cerebrum continuously and selectively, without causing changes in the systemic body temperature even outside of the operation room without any time constraint. Since no liquid is injected into he epidural cavity, the subdural cavity, or the subarachnoid cavity, the internal pressure of the subarachnoid cavity or the brain pressure will not increase even if cooling is continued, and it became possible to continue cooling for any days or any weeks theoretically by merely circulating a heat-cooling medium within the circuit.

Thirdly, it is possible to control the temperature of the spinal cord or the temperature of the brain at the injured site. That the general hypothermia therapy is useful for the injuries to the brain has already been known, at which time, it is thought, "rewarming" from the hypothermia to the normothermia is important in preventing brain injuries. The catheter of the present invention that circulates a heat-cooling medium within the inner space and a device using the same can change the degree of cooling with a heat exchanger, and another advantage is that by changing the flow rate of the heat-cooling medium to be circulated, the degree of cooling the spinal cord or the brain can be changed, and rewarming can be made slowly in stead of quickly. Furthermore, in the case of a catheter in which the heat-cooling medium is not circulated, the degree of cooling the spinal cord, the brain, the esophagus etc. can be changed by controlling the cooling unit or the heat exchanger that are in contact with the heat radiation member of the catheter or by controlling the temperature of the surrounding air.

Fourthly, it can be easily accessed and can be easily controlled. In the case of emergency, the catheter for cooling can be inserted into the epidural cavity, the subdural cavity, or the subarachnoid cavity by puncture with a puncture needle, or by laminectomy, and then it only needs to be connected to the circulating cooling unit, or to a cooling unit, a heat exchanger etc. to cool which automatically and continuously controlling the temperature of the spinal cord, the esophagus etc.

The protection of the spinal cord by the catheter and the device of the present invention can contribute to the treatment of spinal cord disorders containing the prevention of paraplegia in the surgery of thoracoabdominal aortic aneurysm in the clinical settings. Furthermore, they are expected to be effective for injuries of the spinal cord due to traumas to the spinal cord, disorders due to spinal cord compression or stenosis, disorders from tumors, degenerative diseases of the spinal cord (specifically amyotrophic lateral sclerosis (ALS) etc.). Furthermore, the catheter and the device of the present invention are useful for topical cooling the brain selectively without changing the general body temperature, and in the clinical settings they are expected to improve the vital prognosis of patients with brain injuries due to traumas, and alleviate the disorders such as consciousness disorders, paralysis or epilepsy. They are also useful for topical cooling the esophagus selectively without changing the general body temperature, and it is expected that they can alleviate complications as a means for preventing the esophagus injuries that may occur during radiofrequency ablation of the atrium performed as a treatment of atrial fibrillation in the clinical settings.

The invention claimed is:

1. A process for topically cooling a spinal cord of a mammal, comprising the steps of:
   using a catheter having high thermal conductivity and an inner space to circulate a heat-cooling medium therein but has no hole connecting to the outside, wherein said catheter is shaped in a fold-back U form,
   transdermally inserting the catheter into the epidural cavity, the subdural cavity, or the subarachnoid cavity of the spinal cord at one site,
   and circulating the heat-cooling medium in the inner space of the catheter to cool the spinal cord across the dura mater or directly.

2. The process of topically cooling the spinal cord according to claim 1, wherein the catheter topically cools the spinal cord selectively and continuously.

3. The process of topically cooling the spinal cord according to claim 1, wherein the heat-cooling medium is a cooling water or a cooling gas.

4. The process of topically cooling the spinal cord according to claim 1, wherein the catheter is linked and arranged in series to a reservoir for preserving a heat-cooling medium, a pump for delivering said heat-cooling medium, and a heat exchanger for cooling said heat-cooling medium, by a pipe-shaped tube for circulating the heat-cooling medium.

5. The process for topically cooling the spinal cord according to claim 2, wherein the heat-cooling medium is a cooling water or a cooling gas.

6. The process of topically cooling the spinal cord according to claim 2, wherein the catheter is linked and arranged in series to a reservoir for preserving a heat-cooling medium, a pump for delivering said heat-cooling medium, and a heat exchanger for cooling said heat-cooling medium, by a pipe-shaped tube for circulating the heat-cooling medium.

7. The process of topically cooling the spinal cord according to claim 3, wherein the catheter is linked and arranged in series to reservoir for preserving a heat-cooling medium, a pump for delivering said heat-cooling medium, and a heat exchanger for cooling said heat-cooling medium, by a pipe-shaped tube for circulating the heat-cooling medium.

8. The process of topically cooling the spinal cord according to claim 1, wherein the high thermal conductive material of the catheter is stainless, titanium, aluminum, gold, silver, or copper.

* * * * *